(12) United States Patent
Lawinger et al.

(10) Patent No.: US 11,071,557 B2
(45) Date of Patent: Jul. 27, 2021

(54) CATHETER FOR CREATING PULSE WAVE WITHIN VASCULATURE

(71) Applicant: Medtronic Vascular, Inc., Santa Rosa, CA (US)

(72) Inventors: Jason Lawinger, Otsego, MN (US); Cassandra Morris, Plymouth, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 537 days.

(21) Appl. No.: 15/788,582

(22) Filed: Oct. 19, 2017

(65) Prior Publication Data
US 2019/0117242 A1    Apr. 25, 2019

(51) Int. Cl.
*A61B 17/22*    (2006.01)
*A61M 25/10*    (2013.01)
*A61B 18/26*    (2006.01)

(52) U.S. Cl.
CPC .... *A61B 17/2202* (2013.01); *A61B 17/22022* (2013.01); *A61B 18/26* (2013.01);
(Continued)

(58) Field of Classification Search
CPC .......... A61B 17/22022; A61B 17/2202; A61B 17/22004; A61B 2017/22025;
(Continued)

(56) References Cited

U.S. PATENT DOCUMENTS

| 4,445,892 A | 5/1984 | Hussein et al. |
| 5,505,700 A | 4/1996 | Leone et al. |

(Continued)

FOREIGN PATENT DOCUMENTS

| CN | 2614695 Y | 5/2004 |
| CN | 101505822 A | 8/2009 |

(Continued)

OTHER PUBLICATIONS

Rosenschein et al., "Ultrasound Imaging-Guided Noninvasive Ultrasound Thrombolysis: Preclinical Results", Journal of the American Heart Association, vol. 102, Issue 2, Jul. 11, 2000, 8 pp. (Year: 2000).*

(Continued)

*Primary Examiner* — Laura A Bouchelle
*Assistant Examiner* — Anh Bui
(74) *Attorney, Agent, or Firm* — Shumaker & Sieffert, P.A.

(57) ABSTRACT

In some examples, a medical device includes a flexible elongate member configured for navigation through vasculature of a patient to a target treatment site. A distal portion of the elongate member including a first balloon portion that is inflatable to an expanded state, a second balloon portion that is inflatable to an expanded state, and a cavitation generator. When the balloon portions are in their expanded states within the vasculature, a cavity is defined between the elongate member and the target treatment site and exterior to the first and second balloon portions. The cavitation generator is configured to deliver energy to a fluid within the cavity to cause the fluid to undergo cavitation to generate a pressure pulse wave within the fluid.

18 Claims, 8 Drawing Sheets

(52) U.S. Cl.
CPC ...... *A61M 25/104* (2013.01); *A61M 25/1011* (2013.01); *A61B 2017/22008* (2013.01); *A61B 2017/22025* (2013.01); *A61B 2017/22038* (2013.01); *A61B 2017/22054* (2013.01); *A61B 2017/22067* (2013.01); *A61B 2017/22079* (2013.01); *A61M 25/1002* (2013.01); *A61M 2025/105* (2013.01); *A61M 2025/1015* (2013.01); *A61M 2025/1052* (2013.01); *A61M 2025/1079* (2013.01); *A61M 2025/1081* (2013.01)

(58) Field of Classification Search
CPC ........... A61B 2017/22051; A61B 2017/22054; A61M 25/1011; A61M 2025/1052
See application file for complete search history.

(56) References Cited

U.S. PATENT DOCUMENTS

| | | |
|---|---|---|
| 5,779,698 A | 7/1998 | Clayman et al. |
| 6,527,759 B1 | 3/2003 | Tachibana et al. |
| 8,568,399 B2 | 10/2013 | Azamian et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,858,585 B2 | 10/2014 | Stengel |
| 8,888,788 B2 | 11/2014 | Hakala et al. |
| 8,956,352 B2 | 2/2015 | Mauch et al. |
| 8,956,371 B2 | 2/2015 | Hawkins et al. |
| 8,956,374 B2 | 2/2015 | Hawkins et al. |
| 9,011,463 B2 | 4/2015 | Adams et al. |
| 9,044,618 B2 | 6/2015 | Hawkins et al. |
| 9,072,534 B2 | 7/2015 | Adams et al. |
| 9,220,521 B2 | 12/2015 | Hawkins et al. |
| 9,642,673 B2 | 5/2017 | Adams et al. |
| 9,707,036 B2 | 7/2017 | Anderson et al. |
| 9,730,715 B2 | 8/2017 | Adams |
| 2007/0088246 A1* | 4/2007 | Steward ............... A61M 25/104 604/22 |
| 2009/0312768 A1 | 12/2009 | Hawkins et al. |
| 2010/0023088 A1 | 1/2010 | Stack et al. |
| 2010/0114020 A1 | 5/2010 | Hawkins et al. |
| 2010/0114065 A1 | 5/2010 | Hawkins et al. |
| 2012/0116289 A1 | 5/2012 | Hawkins et al. |
| 2012/0221013 A1 | 8/2012 | Hawkins et al. |
| 2013/0030447 A1 | 1/2013 | Adams |
| 2013/0116714 A1* | 5/2013 | Adams ............. A61B 17/22012 606/159 |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0046353 A1 | 2/2014 | Adams |
| 2014/0163592 A1 | 6/2014 | Hawkins et al. |
| 2014/0288570 A1 | 9/2014 | Adams |
| 2015/0039002 A1 | 2/2015 | Hawkins |
| 2016/0008016 A1 | 1/2016 | Cioanta et al. |
| 2016/0135828 A1 | 5/2016 | Hawkins et al. |
| 2016/0184570 A1* | 6/2016 | Grace ................ A61M 25/104 600/435 |
| 2017/0135709 A1* | 5/2017 | Nguyen ........... A61B 17/22022 |
| 2018/0153568 A1 | 6/2018 | Kat-Kuoy |
| 2018/0264247 A1* | 9/2018 | Mantri ..................... A61N 5/00 |

FOREIGN PATENT DOCUMENTS

| | | | |
|---|---|---|---|
| CN | 104582597 A | 4/2015 | |
| CN | 105536123 A | 5/2016 | |
| EP | 0623360 A1 | 11/1994 | |
| EP | 1100385 A1 | 5/2001 | |
| EP | 2848225 A1 | 3/2015 | |
| WO | WO-0007508 A1 * | 2/2000 | ......... A61K 41/0047 |
| WO | 2016064076 A1 | 4/2016 | |
| WO | 2016109736 A1 | 7/2016 | |

OTHER PUBLICATIONS

Robert J Siegel et al., "Percutaneous Ultrasonic Angioplasty: Initial Clinical Experience" Lancet, vol. 334, No. 8666, Sep. 1, 1989, pp. 772-774.

Locke et al., "Electrohydraulic Discharge and Nonthermal Plasma for Water Treatment," Industrial & Engineering Chemistry Research, Dec. 31, 2005, 24 pp.

Siegel et al., "Percutaneous Ultrasonic Angioplasty: Initial Clinical Experience", The Lancet, vol. 334, No. 8666, Sep. 30, 1989, pp. 772-774.

Siegel et al., "In Vivo Ultrasound Arterial Recanalization of Atherosclerotic Total Occlusions", Journal of the American College of Cardiology, vol. 15, Issue 2, Feb. 1990, pp. 345-351.

Rosenschein et al., "Ultrasound Imaging-Guided Noninvasive Ultrasound Thrombolysis: Preclinical Results", Journal of the American Heart Association, vol. 102, Issue 2, Jul. 11, 2000, 8 pp.

Examination Report from counterpart European Application No. 18198829.6, dated Jan. 23, 2020 8 pp.

First Office Action and Search Report, and translation thereof, from counterpart Chinese Application No. 201811221174.5, dated Nov. 25, 2020, 15 pp.

Examination Report from counterpart European Application No. 18198829.6, dated Apr. 20, 2021, 7 pp.

Notice of Second Office Action, and translation thereof, from counterpart Chinese Application No. 2018112211745, dated Apr. 16, 2021, 17 pp.

* cited by examiner

CATHETER FOR CREATING PULSE WAVE WITHIN VASCULATURE

TECHNICAL FIELD

This disclosure relates to medical devices such as a medical catheter.

BACKGROUND

Medical catheters have been proposed for use with various medical procedures. For example, medical catheters may be used to access and treat defects in blood vessels, such as, but not limited to, treatment of calcific atherosclerotic plaque buildup within the vasculature wall of vasculature associated with cardiovascular disease. Some techniques for treating such diseases may include balloon angioplasty alone or balloon angioplasty followed by stenting of the vasculature. However, such techniques may fail to address certain types of plaque buildup and/or result in re-stenotic events.

SUMMARY

In some aspects, the disclosure describes example medical devices, such as catheters, that include one or more occlusion balloons and a cavitation generator configured to deliver energy intravascularly to fluid in contact with a vasculature wall to induce cavitation within the fluid. The cavitation may be used to treat a defect in the vasculature of the patient. For example, the cavitation may produce a high-energy pressure pulse wave that, when directed at a vasculature wall, may be used to disrupt and fracture calcific atherosclerotic plaque buildup within the vasculature wall. The disruption and facture of the plaque may allow the vasculature to be more easily expanded to achieve better blood flow through the vessel. In some examples, the use of such devices may reduce or eliminate the need for subsequent stenting of the vasculature and reduce the chance of restenosis. In some other aspects, the disclosure describes methods of using the medical devices described herein.

Clause 1: In one example, a medical device includes a flexible elongate member including a distal portion configured to be navigated though vasculature of a patient to a target treatment site; a first balloon portion connected to the flexible elongated member, the first balloon portion is inflatable to an expanded state to occlude a proximal portion of the vasculature proximal to the target treatment site; a second balloon portion connected to the flexible elongated member, the second balloon portion is inflatable to an expanded state to occlude a distal portion of the vasculature distal to the target treatment site, and when the first and second balloon portions are in the respective expanded states within the vasculature, a cavity is defined between the flexible elongate member and the target treatment site, the cavity being exterior to the first and second balloon portions; and a cavitation generator configured to deliver energy to a fluid within the cavity to cause the fluid to undergo cavitation to generate a pressure pulse wave within the fluid.

Clause 2: In some of the examples of the medical device of clause 1, the medical device includes a delivery catheter configured to deliver the fluid to the cavity.

Clause 3: In some of the examples of the medical device of clause 1 or 2, the delivery catheter is configured to aspirate the cavity prior to delivering the fluid.

Clause 4: In some of the examples of the medical device of any of clauses 1 to 3, the medical device includes a connective segment defining a connective lumen, the connective lumen providing a fluid connection between the first and second balloon portions.

Clause 5: In some of the examples of the medical device of any of clauses 1 to 4, the medical device includes a single balloon including the first balloon portion, the second balloon portion, and the connective segment, the single balloon having a dumbbell shape, the first and second balloon portions corresponding to lobes of the dumbbell shape.

Clause 6: In some of the examples of the medical device of any of clauses 1 to 5, the medical device includes a treatment balloon positioned over the flexible elongated member, the treatment balloon being inflatable within the cavity to expand the vasculature after delivery of the pressure pulse wave by the cavitation generator.

Clause 7: In some of the examples of the medical device of clause 6, the medical device includes a retractable sheath disposed over the treatment balloon, the retractable sheath being configured to be retracted to expose the treatment balloon after the delivery of the pressure pulse wave by the cavitation generator.

Clause 8: In some of the examples of the medical device of clause 6 or 7, the treatment balloon includes at least one of an anti-restenotic agent, an anti-proliferative agent, or an anti-inflammatory agent.

Clause 9: In some of the examples of the medical device of any of clauses 1 to 8, the cavitation generator includes a plurality of electrodes configured to deliver an electrical signal to the fluid within the cavity to induce the cavitation within the fluid.

Clause 10: In some of the examples of the medical device of clause 9, the medical device includes a guidewire, the flexible elongate member defines a lumen configured to receive the guidewire, and the guidewire forms an electrode of the plurality of electrodes.

Clause 11: In some of the examples of the medical device of clause 9 or 10, the flexible elongate member defines at least one opening through a sidewall of the flexible elongate member, the at least one opening exposes an electrically conductive surface of the guidewire to the fluid within the cavity, and the electrically conductive surface of the guidewire forms an electrode of the plurality of electrodes.

Clause 12: In some of the examples of the medical device of any of clauses 9 to 11, at least two of the plurality of electrodes are moveable relative to each other.

Clause 13: In some of the examples of the medical device of any of clauses 1 to 12, the cavitation generator includes an optical fiber laser or a piezoelectric transducer.

Clause 14: In some of the examples of the medical device of clause 13, the optical fiber laser or the piezoelectric transducer is movable relative to the flexible elongate member.

Clause 15: In some of the examples of the medical device of any of clauses 1 to 14, at least a portion of the cavitation generator is positioned within the cavity and exterior to the first and second balloon portions.

Clause 16: In some of the examples of the medical device of any of clauses 1 to 15, the medical device includes a signal generator configured to generate and deliver the energy to the fluid within the cavity via the cavitation generator.

Clause 17: In some of the examples of the medical device of clause 16, the signal generator is configured to deliver a plurality of energy pulses in the form of electrical or photonic energy, the energy pulses having a pulse width of about between about 1 nanosecond and about 20 nanoseconds.

Clause 18: In some examples, a method including introducing a catheter through vasculature of a patient to a target treatment site, the catheter including: a flexible elongate member including a distal portion configured to be navigated though the vasculature of the patient; a first balloon portion connected to the flexible elongated member; a second balloon portion connected to the flexible elongated member and distal to the first balloon portion; and a cavitation generator. The method further includes inflating the first and second balloon portions to an expanded state, the first balloon portion occludes a proximal portion of the vasculature proximal to the target treatment site and the second balloon portion occludes a distal portion of the vasculature distal to the target treatment site, the first and second balloon portions in the respective expanded states within the vasculature form a cavity defined between the flexible elongate member and the target treatment site, the cavity being exterior to the first and second balloon portions; filling the cavity with a fluid; and delivering energy to the fluid within the cavity with the cavitation generator to cause the fluid to undergo cavitation to generate a pressure pulse wave within the fluid.

Clause 19: In some of the examples of the method of clause 18, inflating the first and second balloon portions includes inflating the first balloon portion prior to inflating the second balloon portion.

Clause 20: In some of the examples of the method of clause 18, inflating the first and second balloon portions includes inflating the second balloon portion prior to inflating the first balloon portion.

Clause 21: In some of the examples of the method of clause 18, inflating the first and second balloon portions includes simultaneously inflating the first balloon portion and the second balloon portion.

Clause 22: In some of the examples of the method of any of clauses 18 to 21, the cavitation generator includes a plurality of electrodes, and delivering the energy to the fluid within the cavity includes delivering an electrical signal to the fluid via the plurality of electrodes to induce cavitation within the fluid.

Clause 23: In some of the examples of the method of clause 22, at least one of the electrodes of the plurality of electrodes is defined by a portion of a guidewire, and delivering the electrical signal includes delivering the electrical signal between the guidewire and at least one other electrode of the plurality of electrodes.

Clause 24: In some of the examples of the method of any of clause 22 or 23, delivering the electrical signal includes delivering a plurality of electrical pulses having a pulse width of about 1 microsecond to about 5 microseconds.

Clause 25: In some of the examples of the method of any of clauses 18 to 24, the cavitation generator includes an optical fiber laser, delivering the energy to the fluid within the cavity includes delivering photonic energy with the optical fiber laser to heat the fluid, the photonic energy being configured to induce the cavitation within the fluid.

Clause 26: In some of the examples of the method of clause 25, delivering the photonic energy includes delivering plurality of photonic pulses, the plurality of photonic pulses defines a pulse width between about 1 nanosecond and about 20 nanoseconds and a pulse frequency of about 10 milliseconds to about 10 seconds.

Clause 27: In some of the examples of the method of any of clauses 18 to 26, the catheter further includes a treatment balloon positioned over the flexible elongated member, and the method includes inflating the treatment balloon to expand the vasculature after a pressure pulse wave therapy has been performed by the cavitation generator.

Clause 28: In some of the examples of the method of any of clauses 18 to 27, the method further includes aspirating the cavity formed by the first and second balloon portions before or while filling the cavity with the fluid.

Clause 29: In some of the examples of the method of any of clauses 18 to 28, the method further includes aspirating the fluid from the cavity, deflating the first and second balloon portions, and removing the catheter from the vasculature of the patient.

The details of one or more examples are set forth in the accompanying drawings and the description below. Other features, objects, and advantages of examples according to this disclosure will be apparent from the description and drawings, and from the claims.

DETAILED DESCRIPTION

This disclosure describes medical devices, such as intravascular catheters, that include a relatively flexible elongated member (e.g., the body of the catheter) configured to be navigated through vasculature of a patient to a target treatment site within the vasculature, and first and second balloon portions connected to the elongated member. The first and second balloon portions are inflatable to an expanded state to occlude portions of the vasculature proximal and distal to the target treatment site, respectively, to define a cavity between the flexible elongate member and the vasculature wall that is exterior to both of the first and second balloon portions. The medical device further includes a cavitation generator configured to deliver energy to a fluid within the cavity to cause the fluid to undergo cavitation and generate a high-energy pressure pulse wave within the fluid. The pulse wave may be used to treat a defect in the vasculature of the patient at the target treatment site.

In some examples, the target treatment site may be a site within the vasculature that has a defect that may be affecting blood flow through the vasculature. For example, the target treatment site may be a portion of the vasculature wall that includes a calcified lesion, e.g., calcific atherosclerotic plaque buildup. A calcified lesion can cause partial or full blockages of blood bearing vasculatures, which can result in adverse physiological effects to the patient. Such lesions may be very hard and difficult to treat using traditional methods, such as balloon angioplasty, stenting, thrombectomy, atherectomy, or other interventional procedures.

The medical devices described herein are primarily referred to as catheters, but can include other medical devices, that are designed to deliver energy to a fluid in contact with the vasculature wall at the target treatment site to induce cavitation of the fluid.

In some examples, a cavitation generator may include a plurality of electrodes configured to deliver an electrical signal through the fluid in the cavity defined between the flexible elongate member and the vasculature wall, and between (but external to) the first and second balloon portions. In other examples, the cavitation generator may include an optical fiber laser configured to deliver photonic energy to the fluid in the cavity or may include a piezoelectric transducer that uses ultrasound to generate energy within the fluid to produce the cavitation. The energy transmitted to the fluid (e.g., electrical, photonic, or ultrasonic energy) may rapidly heat the fluid to produce a short-lived gaseous steam/plasma bubble within the fluid that quickly collapses (e.g., cavitates), releasing energy in the form of a pressure pulse wave. The pressure pulse wave may impact the calcified lesion (or other defect at the treatment site) to fracture or disrupt at least part of the lesion. This treatment of the calcified lesion may be used in conjunction with a treatment balloon to help open-up the blood vessel of the patient, improving blood flow in the blood vessel. For example, the treatment of the calcified lesion using the medical devices described herein may help restore the vasculature to a normal or at least increased flow diameter.

Figure 1:
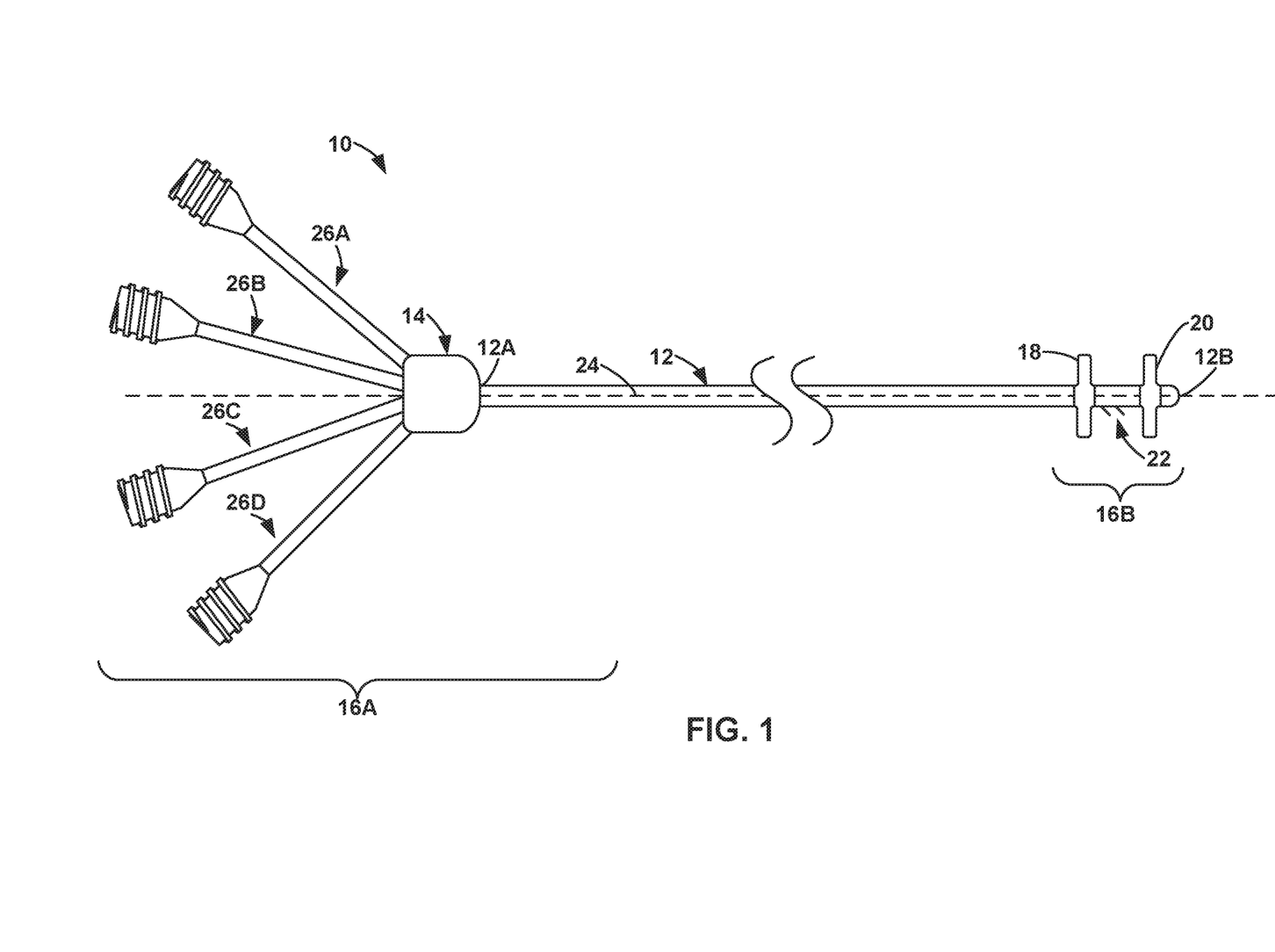
FIG. 1 is a schematic side view of an example catheter that includes a flexible elongate member with a distal portion that includes first and second balloon portions and cavitation generator.

FIG. 1 is a schematic side view of an example catheter 10, which includes a flexible elongate member 12 extending from proximal end 12A to distal end 12B, with the side view of FIG. 1 is taken along a longitudinal axis 24 of flexible elongate member 12. Catheter 10 includes a hub 14 connected to proximal end 12A of flexible elongate member 12. Hub 14 including proximal end 12A form part of a proximal portion 16A of catheter 10. Catheter 10 also includes a distal portion 16B that include distal end 12B of flexible elongate member 12. Distal portion 16B also includes a first balloon portion 18, a second balloon portion 20, and a cavitation generator 22 (e.g., the component(s) or portions of the component(s) intended to directly contact a fluid to induce cavitation of the fluid). The designations proximal and distal portion 16A and 16B are used to describe different regions of catheter 10 and may be of any suitable length. Elongate member 12 may also be characterized as having one or more intermediate portions separating the proximal and distal portions 16A and 16B.

In some examples, catheter 10 may include a hub 14 positioned at proximal portion 16A. Proximal end 12A of elongate member 12 is received within hub 14 and can be mechanically connected to hub 14 via an adhesive, welding, or another suitable technique or combination of techniques. Hub 14 may include one or more supply tubes 26A, 26B, 26C, 26D (collectively "supply tubes 26"). Supply tubes 26 may provide access to various components of distal portion 16B of elongated flexible elongate member 12 and may be used for passing various components through elongate member 12 (e.g., a guidewire, conductive fluid, or the like). For example, one or more of supply tubes 26 may define a lumen that extends through elongate member 12 to one or both of first balloon portion 18 and second balloon portion 20 for inflating the balloon portion with a fluid to cause the respective balloon portion to expand. One or more of supply tubes 26 may also be configured to introduce a guidewire in a lumen of elongated member 12, deliver energy to cavitation generator 22, aspirate of the vasculature of the patient, deliver a fluid to the target treatment site for the cavitation procedure, and the like.

In some examples, catheter 10 may include a strain relief body (not shown), which may be a part of hub 14 or may be separate from hub 14. Additionally or alternatively, proximal portion 16A of catheter 10 can include another structure in addition or instead of hub 14. For example, catheter hub 14 may include one or more luers or other mechanisms for establishing connections between catheter 10 and other devices.

In some examples, flexible elongate member 12 of catheter 10 may be used to access relatively distal vasculature locations in a patient or other relatively distal tissue sites (e.g., relative to the vasculature access point). Example vasculature locations may include, for example, locations in a coronary artery, peripheral vasculature (e.g., carotid, iliac, or femoral artery, or a vein), or cerebral vasculature. In some examples, flexible elongate member 12 is structurally configured to be relatively flexible, pushable, and relatively kink- and buckle-resistant, so that it may resist buckling when a pushing force is applied to a relatively proximal portion of catheter 10 to advance flexible elongate member 12 distally through vasculature, and so that it may resist kinking when traversing around a tight turn in the vasculature. Unwanted kinking and/or buckling of flexible elongate member 12 may hinder a clinician's efforts to push the catheter body distally, e.g., past a turn in the vasculature.

Flexible elongate member 12 has a suitable length for accessing a target tissue site within the patient from a vasculature access point. The length may be measured along the longitudinal axis of flexible elongate member 12. The working length of flexible elongate member 12 may depend on the location of the lesion within vasculature. For example, if catheter 10 is a catheter used to access a coronary, carotid, or abdominal artery, flexible elongate member 12 may have a working length of about 50 centimeters (cm) to about 200 cm, such as about 110 cm, although other lengths may be used. In other examples, or for other applications, the working length of flexible elongate member 12 may have different lengths.

The outer diameter of flexible elongate member 12 may be of any suitable size or dimension including, for example, between about 1 millimeter (mm) and about 11.3 mm. In some examples, the outer diameter may be substantially constant (e.g., uniform outer diameter), tapered (e.g. tapered or step change to define a narrower distal portion), or combinations thereof. In some examples, flexible elongate member 12 of catheter 10 may have a relatively smaller outer diameter which may make it easier to navigate through a tortuous vasculature.

In some examples, at least a portion of an outer surface of flexible elongate member 12 may include one or more coatings, such as, but not limited to, an anti-thrombogenic coating, which may help reduce the formation of thrombi in vitro, an anti-microbial coating, and/or a lubricating coating. In some examples, the entire working length of flexible elongate member 12 is coated with the hydrophilic coating. In other examples, only a portion of the working length of flexible elongate member 12 coated with the hydrophilic coating. This may provide a length of flexible elongate member 12 distal to hub 14 with which the clinician may grip flexible elongate member 12, e.g., to rotate flexible elongate member 12 or push flexible elongate member 12 through vasculature. In some examples, the entire working length of flexible elongate member 12 or portions thereof may include a lubricious outer surface, e.g., a lubricious coating. The lubricating coating may be configured to reduce static friction and/or kinetic friction between flexible elongate member 12 and tissue of the patient as flexible elongate member 12 is advanced through the vasculature.

In some examples, flexible elongate member 12 may include one or more radiopaque markers which may help a clinician determine the positioning of flexible elongate member 12 relative to relative to a target treatment site. For example, one or more radiopaque markers may be positioned proximal or distal to first balloon portion 18, proximal or distal to second balloon portion 20, in between first and second balloon portions 18, 20, adjacent to cavitation generator 22, or combinations thereof.

Figure 2:
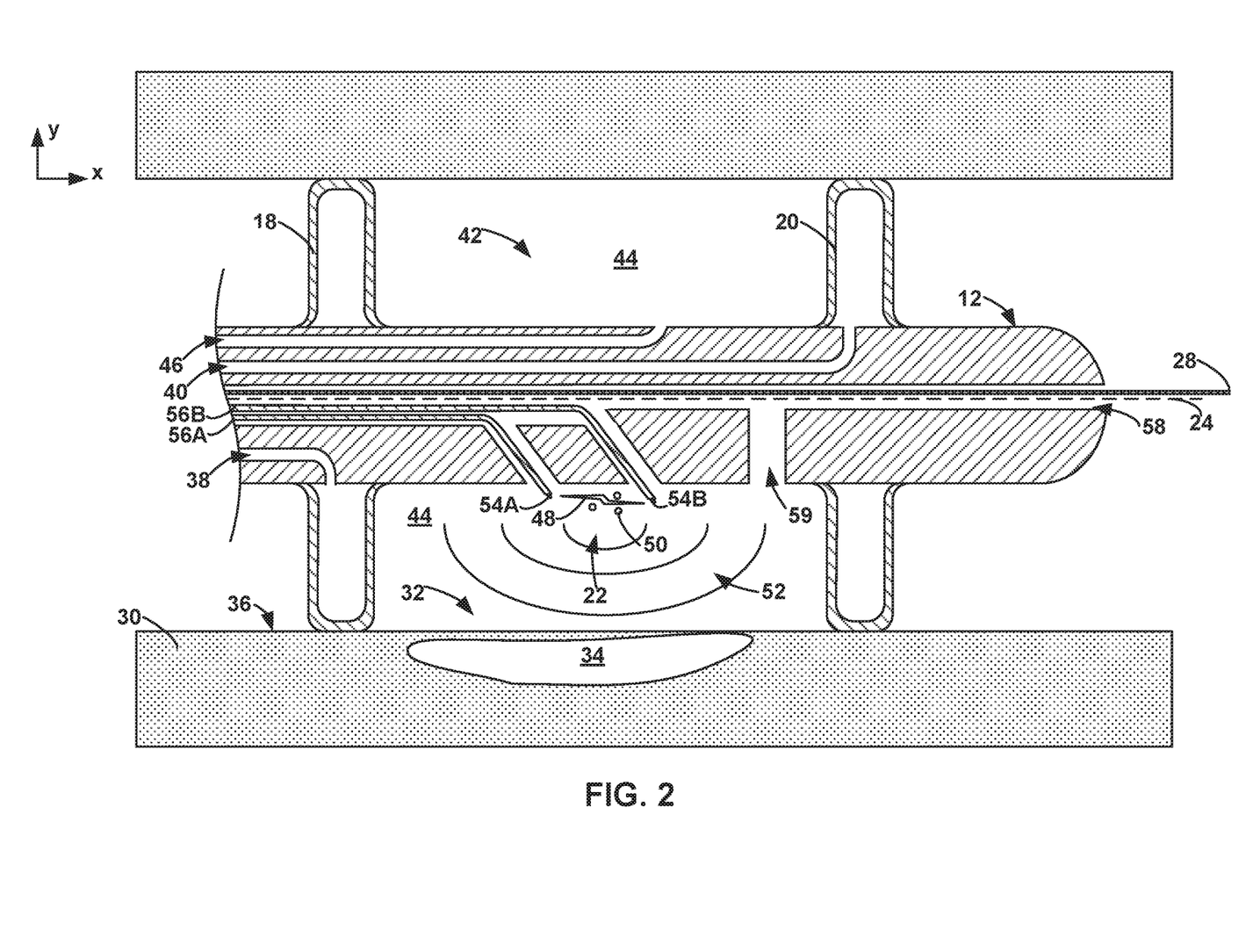
FIG. 2 is an enlargement of the distal portion of the catheter of FIG. 1 with the first and second balloon portions in respective expanded states within vasculature of a patient.

FIG. 2 is an enlarged conceptual cross-sectional view of distal portion 16B of FIG. 1 taken along longitudinal axis 24 of flexible elongate member 12. FIG. 2 shows distal portion 16B deployed within vessel 30 of a patient, vessel 30 including a target treatment site 32 containing a calcified lesion 34 on or within the wall 36 of vessel 30. The location of lesion 34 in FIG. 2 is one example, and lesion 34 may be have another location on or within the wall 36 in other examples.

Distal portion 16B of flexible elongate member 12 includes first balloon portion 18 and second balloon portion 20 mechanically connected to flexible elongate member 12. First balloon portion 18 is mechanically connected to flexible elongate member 12 at a position proximal to second balloon portion 20. Thus, first balloon portion 18 may be referred to as a proximal balloon portion and second balloon portion 20 may be referred to as a distal balloon portion. Balloon portions 18, 20 are each configured to be expanded from a deflated stated to an expanded state via an inflation fluid delivered to the respective balloon via an inflation lumen of elongate body 12. In the example of catheter 10 shown in FIG. 2, each balloon portion 18, 20 may be inflated via a respective inflation lumen 38, 40, which may be accessed via one or more of supply tubes 26 (FIG. 1). In some examples, inflating first and second balloon portions 18, 20 independently may useful to ensure each balloon is balloon is expanded properly to confirms to the contours of the vessel wall 36. Additionally, as discussed further below, inflating first and second balloon portions 18, 20 independently may allow for a portion of the blood between first and second balloon portions 18, 20 to be removed prior to both balloon portions being fully expanded. In other examples of catheter 10, balloon portions 18, 20 can be inflated via the same inflation lumen or fluidically connecting channel.

In the respective expanded states within vessel 30, balloon portions 18, 20 inflate and conform to engage with vessel wall 36 to occlude vessel 30. In its expanded state, first balloon portion 18 engages with vessel wall 36 at a position proximal to target treatment site 32 and occludes vessel 30 to prevent blood from flowing through vessel 30 during a cavitation procedure. In its expanded state, second balloon portion 20 engages with vessel wall 36 at a position distal to target treatment site 32 and occludes vessel 30 to create cavity 42 at target treatment site 32 that can be filled with a conductive fluid and be used for the cavitation procedure.

First and second balloon portions 18, 20 may each include a flexible polymeric material that forms a tight seal with elongate member 12. In some examples, first and second balloon portions 18, 20 may be formed separate of elongate member 12 and attached to an exterior surface of elongate member 12 via co-extrusion, bonding, adhesives, or the like. In other examples, first and second balloon portions 18 may be integrally formed with elongate member 12 such that one or both balloon portions are emended or at least partially embedded in elongate member 12. First and second balloon portions 18, 20 may also be of any suitable size or shape. In some examples, first and second balloon portions 18, 20 may be the same sizes or shapes, while in other examples first and second balloon portions 18, 20 may be different sizes or shapes. Constructing catheter 10 to include balloon positions of different sizes or shape may be useful where catheter 10 is deposed within a vessel with an irregular configuration.

First and second balloon portions 18, 20 may be constructed using any suitable flexible polymeric material including, for example, nylon 12, polyethylene, polyethylene terephthalate (PET), silicone, polyvinyl chloride, polypropylene, polyurethanes, polyamides, polyesters, latex, natural rubber, synthetic rubber, polyether block amides, or the like. Additionally or alternatively first and second balloon portions 18, 20 may be constructed with an electrically insulative material.

When both first and second balloon portions 18, 20 are inflated to the respective expanded states and engage vessel wall 36, first and second balloon portions 18, 20 form a cavity 42. Cavity 42 is formed by vessel wall 36 and the exterior surfaces of first and second balloon portions 18, 20 when first and second balloon portions 18, 20 are inflated in vessel 30. Fluid 44 may be contained within cavity 42 by the vessel wall 36 and the exterior surfaces of first and second balloon portions 18, 20 such that fluid 44 is in direct contact with vessel wall 36. In some examples, cavity 42 may define a tubular shape that encircles the exterior surface of distal portion 16B, limited by first and second balloon portions 18, 20 and vessel wall 36.

In some examples, first and second balloon portions 18, 20 may be independent balloons completely separated from one another and connected to elongate member 12 that are filled to their expanded states independently via separate lumens 38, 40 to form cavity 42. In other examples, first and second balloon portions 18, 20 are in fluid communication with each other, e.g., may be portions of a common balloon or separate balloons that are in fluid communication with each other via a common inflation lumen. For example, elongate member 12 may include a connective segment defining a connective lumen (e.g., connective lumen 86 of FIG. 4) that provides a fluid connection between first and second balloon portions 18, 20. In such examples, first and second balloon portions 18, 20 may be filled simultaneously using the connective lumen (e.g., connective lumen 86 of FIG. 4) to produce cavity 42 (e.g., cavity 84 of FIG. 4). In yet other examples, as described further below with respect to FIG. 5, first and second balloon portions 18, 20 may represent different lobes of the same balloon (e.g., first balloon portion 18 representing a first lobe and second balloon portion 20 representing a second lobe of a single balloon) with the connective lumen being defined by a part of the balloon between the lobes (e.g., connective lumen 116 of FIG. 5). As the two lobes inflate and engage with vessel wall 36, the lobes define cavity 42 (e.g., cavity 112 of FIG. 5) between catheter 10 and vessel wall 36.

Cavity 42 may be filled with a fluid 44 capable of undergoing cavitation via energy delivered to fluid 44 by cavitation generator 22. In some examples, fluid 44 may be or include residual blood within vessel 30 confined within cavity 42 by first and second balloon portions 18, 20. In addition to or instead of the residual blood, in other examples, fluid 44 may be or otherwise include a fluid introduced into cavity 42, such as, but not limited to, saline. In these examples, fluid 44 includes fluid not found in the patient's body, but, rather, introduced into cavity 42 by a clinician. In examples in which fluid 44 is introduced into cavity 42, fluid 44 may be introduced into cavity 44 using any suitable technique. In some examples, elongate member 12 defines a lumen 46 configured to provide access to cavity 42. Lumen 46 may permit the delivery of fluid 44, such as saline, to cavity 42 via one of supply tubes 26. Saline may more readily undergo cavitation compared to blood, thereby requiring less energy to induce cavitation within cavity 42.

Any suitable fluid 44 may be introduced into cavity 42 for the cavitation procedure. Example fluids 44 may include, but are not limited to, biocompatible fluids such as saline or similar solution with a salt content between about 0.9 weight percent (wt. %) and about 5 wt. %; contrast media (e.g., about 25 volume percent (vol. %) to about 75 vol. % contrast media), or the like. The higher the salt content of the saline fluid, the higher the conductance will be for the fluid, thereby requiring less energy to increase the temperature of the fluid and induce cavitation. Additionally, the higher the concentration of contrast media, the more viscous fluid 44 will be leading to a higher dissipation of the cavitation bubbles. In some examples, fluid 44 may be heated (e.g., body temperature or about 37° C.) prior to introduction into cavity 42. Heating fluid 44 may increase the relative vapor pressure of the fluid and thus require less energy to induce cavitation.

In some such examples, lumen 46 may also be configured to aspirate cavity 42 to remove blood or fluid 44 (e.g., pre or post cavitation) as part of the cavitation procedure. For example, a vacuum source may be connected to one of supply tubes 26 to cause a fluid within cavity 42 to be suctioned from the cavity via lumen 46. Additionally or alternatively, flexible elongate member 12 may define a different lumen (e.g., a lumen other than lumen 46) with access to cavity 42 for purposes of aspirating cavity 42, or catheter 10 may be used in conjunction with an aspiration catheter.

Distal portion 16B of catheter 10 also includes cavitation generator 22 configured to deliver energy to fluid 44 within cavity 42 to cause fluid 44 to undergo cavitation. The term "cavitation generator" may refer to the component(s) or portions of the component(s) that are used induce cavitation within cavity 42 and is not intended to imply that the entire cavitation system is include in cavity 42. For example, while cavitation generator 22 may refer to conductors, a fiber optic laser, a piezoelectric transducer, or the like position in cavity 42, it is understood that the energy source for such componentry may not be located within cavity 42 and may be exterior to the body of a patient.

During the cavitation procedure, energy 48 in the form of, for example, an electrical signal or photonic energy may be delivered to fluid 44 via cavitation generator 22 to heat a portion of fluid 44 to generate a steam/plasma bubbles 50 within fluid 44. The steam/plasma bubbles 50 may represent relatively low-pressure pockets of vapor generated from the surrounding fluid 44. The low-pressure steam/plasma bubbles 50 eventually collapse in on themselves due to the relatively high pressure of the surrounding fluid 44 and heat loss of the steam/plasma bubbles 50 to the surrounding fluid 44. As steam/plasma bubbles 50 collapse, the bubbles release a large amount of energy in the form of a high-energy pressure pulse wave 52 within fluid 44. In some examples, the formation and subsequent collapse of the steam/plasma bubbles 50 may be short lived or nearly instantaneous, causing the pressure pulse waves 52 to originate near the source of energy 48.

Pressure pulse waves 52 propagate through fluid 44 where they impact vessel wall 36 transmitting the mechanical energy of pressure pulse wave 52 into the tissue of vessel 30 and calcified lesion 34 on or within vessel wall 36. The energy transmitted to calcified lesion 34 may cause the lesion to fracture or break apart allowing vessel 30 to be subsequently expanded (e.g., via balloon expansion) to a larger flow diameter.

By conducting the cavitation procedure in vessel 30 within fluid 44 in direct and intimate contact with vessel wall 36, the transfer of energy from pressure pulse waves 52 to calcified lesion 34 may be more efficient as compared to a cavitation procedure that introduces one or more intermediate devices, such as a balloon, between the source of cavitation (e.g., energy 48) and calcified lesion 34. In some examples, the improved efficiency of the process may require less energy 48 to be transmitted to fluid 44 to incur the same amount of cavitation. Further, as the temperature of fluid 44 will increase as a consequence of the cavitation procedure, reducing the overall energy 48 delivered to fluid 44 may also help reduce the temperature increase to fluid 44 caused by the delivery of energy 48 to fluid 44. The more efficient transfer of energy from pressure pulse waves 52 to calcified lesion 34 may also reduce the duration of which the cavitation procedure must be performed in order to sufficiently fracture or break apart calcified lesion 34 resulting in an overall shorter procedure. Additionally or alternatively, due to the improved efficiency of the cavitation process, the profile of catheter 10 may be reduced. For example, the lower power requirements mean that the components powering cavitation generator 22 (e.g., conductors, fiber optic lasers, or piezoelectric transducers) may require a lower energy load thereby allowing for smaller gauge of component to be incorporated into catheter 10. In some examples, the lowered power demands may also permit catheter 10 and the associate energy source to be operated as a handheld unit.

Cavitation generator 22 may include any suitable device configured to deliver energy to fluid 44 within cavity 42 to cause fluid 44 to undergo cavitation. As shown in the example of FIG. 2, cavitation generator 22 may include a plurality of electrodes 54A, 54B positioned in cavity 42, e.g., in direct contact with fluid 44. Although two electrodes are shown in FIG. 2, in other examples more than two electrodes may be present. Energy 48 may represent an electrical signal that forms a corona, an electrical arc, a spark, or the like between a pair of plurality of electrodes 54A, 54B using fluid 44 as a conductive media. Energy 48 in the form of corona, electrical arc, spark, or the like causes fluid 44 to form gaseous steam/plasma bubbles 50 within fluid 44 that may nucleate and cavitate near electrodes 54A, 54B.

The electrical signal transmitted and received between plurality of electrodes 54A, 54B may be delivered to electrodes 54A, 54B from an energy source separate from catheter 10 by one or more conductors 56A, 56B extending within elongate member 12 from proximal portion 16A of catheter 10 to one or more of plurality of electrodes 54A, 54B. In the example shown in FIG. 2, conductors 56A, 56B are electrically connected to respective electrodes 54A, 54B. For example, electrodes 54A, 54B may represent a portion of the respective conductor 56A, 56B that is exposed to fluid 44 within cavity 42. In other examples, electrodes 54A, 54B may be formed separate from conductors 56A, 56B and electrically and mechanically connected to conductors 56A, 56B.

Figure 3:
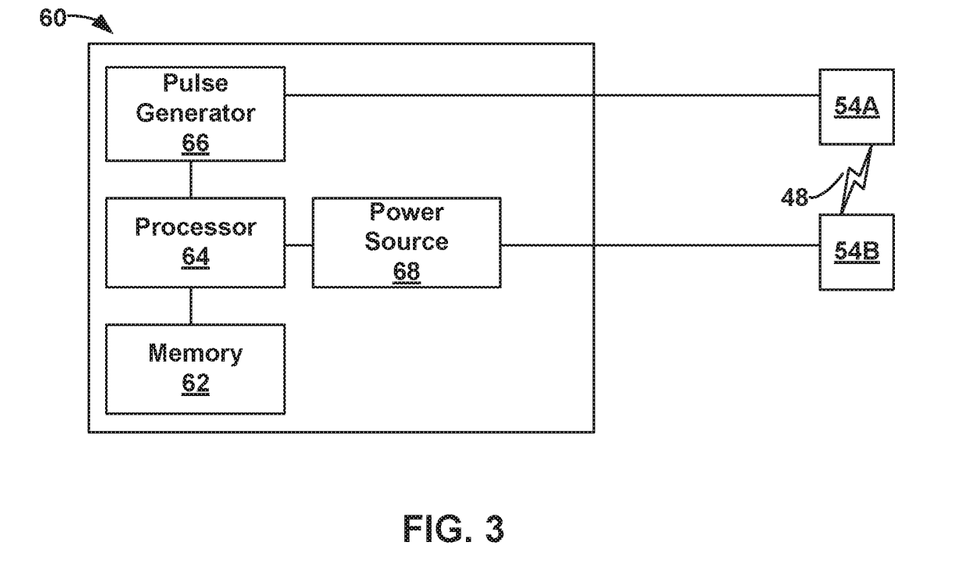
FIG. 3 is a schematic block diagram of an example cavitation energy source that may be used with the catheter of FIG. 1 to induce cavitation of within a fluid.

A proximal end of conductors 56A, 56B may be electrically connected to an energy source, an example of which is shown in FIG. 3, in order to electrically connect electrodes 54A, 54B to the energy source. For example, the proximal end of conductors 56A, 56B may extend through supply tubes 26 or may be connected to electrical contacts at or near proximal end 16A of catheter 10. The electrical contacts may then be directly electrically connected to the energy source or electrically connected to the energy source via a lead or another suitable electrical conductor.

Conductors 56A, 56B and electrodes 54A, 54B may be formed using any suitable electrically conductive material including, for example, titanium alloys (e.g., Ti—Mo alloy), platinum or platinum-iridium alloys, stainless steel, copper, copper alloys (e.g., copper and hafnium or tungsten), tungsten, or the like. In some examples, conductors 56A, 56B and electrodes 54A, 54B may be formed of the same material, while in other examples conductors 56A, 56B and electrodes 54A, 54B may be formed of different materials. For example, conductors 56A, 56B may be formed using metal wires electrically insulated from one another and extending along longitudinal axis 24. In such examples, the materials and design of the conductors 56A, 56B may be selected such that conductors 56A, 56B do not significantly impede or hinder the navigability of catheter 10. Conductors 56A, 56B may be electrically coupled to electrodes 54A, 54B.

In some examples, one or more electrodes of plurality of electrodes 54A, 54B may be repositionable with cavity 42, e.g., may be movable to change a distance between two or more electrodes 54A, 54B. The mobility of electrodes 54A, 54B may allow a clinician to reposition the electrodes 54A, 54B relative to each other, deliver the cavitation energy 48 (e.g., corona or arc) at a certain position within cavity 42, modify the magnitude of the pressure pulse wave generated, or the like. Additionally or alternatively, in examples in which plurality of electrodes 54A, 54B include more than two electrodes, the maneuverability of one or more of the respective electrodes relative to each other may allow the clinician select and position a specific set of electrodes for delivering cavitation energy 48.

In other examples, one or more of electrodes 54A, 54B may be fixed relative to elongate member 12 or form part of the exterior surface of elongate member 12. In examples where first and second balloon portions 18, 20 help center elongate member 12 within vessel 30, having one or more of electrodes 54A, 54B remain immobile relative to elongate 12 may help ensure that the cavitation occurs towards the center of vessel 30.

Flexible elongate member 12 may define a guidewire lumen 58 configured to receive guidewire 28. Guidewire 28 may be any suitable guide member configured to aid navigation of catheter 10 to target treatment site 32. For example, guidewire 28 may be introduced through vasculature of a patient to target treatment site 32 and distal portion 16B of catheter 10 may be advanced over guidewire 28 to navigate flexible elongate member 12 through the vasculature of the patient to target treatment site 32. In some examples in which cavitation generator 22 includes a plurality of electrodes 54A, 54B, one of the electrodes may be formed by a guidewire 28. For example, flexible elongate member 12 may define one or more ports 59 through the sidewall of flexible elongate member 12 that exposes a surface of guidewire 28 to the fluid 44 within cavity 42. In such examples, guidewire 28 may be an electrode used to deliver energy 48 to fluid 44 to induce cavitation of fluid 44. For example, guidewire 28 may function as a reference electrode with a proximal end connected to an energy source external to the patient. In such examples, guidewire 28 may be fully electrically insulated or at least partially electrically insulated (e.g., insulated over at least the exposed proximal portion of the guidewire). In some examples in which guidewire 28 functions as an electrode used with a cavitation procedure, catheter 10 may be constructed with only one of electrodes 54A, 54B, and guidewire 28 (or a portion thereof) may be the second electrode.

In some examples in which energy 48 is electrical energy delivered between plurality of electrodes 54A, 54B, the intensity of pressure pulse waves 52 may be adjusted by controlling the intensity of the electrical signal delivered via electrodes 54A, 54B, the separation distance between electrode 54A, 54B, a surface area of electrodes 54A, 54B, and the like. The intensity of the electrical signal may be function of one or more of a voltage, a current, a frequency (e.g., a pulse rate in the case of pulses), a pulse width, or one or more other electrical signal parameters.

FIG. 3 shows a schematic block diagram of an example energy source 60 that may be used with catheter 10 to induce cavitation within fluid 44. Energy source 60 includes memory 62, processing circuitry 64, electrical signal generator 66, and power source 68. Processing circuitry 64 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 64. The functions attributed to processors described herein, including processing circuitry 64, may be provided by a hardware device and embodied as software, firmware, hardware, or any combination thereof.

Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processing circuitry 64, cause processing circuitry 64 to perform various functions described herein. Memory 62 may be considered, in some examples, a non-transitory computer-readable storage medium including instructions that cause one or more processors, such as, e.g., processing circuitry 64, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from energy source 60, and moved to another device. In certain examples, a non-transitory storage medium may store data that can, over time, change (e.g., in RAM).

Processing circuitry 64 is configured to control energy source 60 and electrical signal generator 66 to generate and deliver an electrical signal to plurality of electrodes 54A, 54B via conductor 56A, 56B to induce cavitation of fluid 44. Electrical signal generator 66 includes electrical signal generation circuitry and is configured to generate and deliver an electrical signal in the form of pulses and/or a continuous wave electrical signal. In the case of electrical pulses, electrical signal generator 66 may be configured to generate and deliver pulses having an amplitude of about 500 volts (V) to about 4000 V, a pulse width of about 1 microsecond to about 5 microseconds, and a frequency of about 0.5 Hertz (Hz) to about 5 Hz. In some examples in which catheter 10 includes more than two electrodes 54A, 54B, processing circuitry 64 controls electrical signal generator 66 to generate and deliver multiple electrical signals via different combinations of electrodes. In these examples, energy source 60 may include a switching circuitry to switch the delivery of the electrical signal across different electrodes, e.g., in response to control by processing circuitry 64. In other examples, electrical signal generator 66 may include multiple current sources to drive more than one electrode combination at one time.

Power source 68 delivers operating power to various components of energy source 60. In some examples, power source 68 may represent hard-wired electrical supply of alternating or direct electrical current. In other examples, power source 68 may include a small rechargeable or non-rechargeable battery and a power generation circuit to produce the operating power. Recharging may be accomplished through proximal inductive interaction between an external charger and an inductive charging coil within energy source 60.

Figure 4:
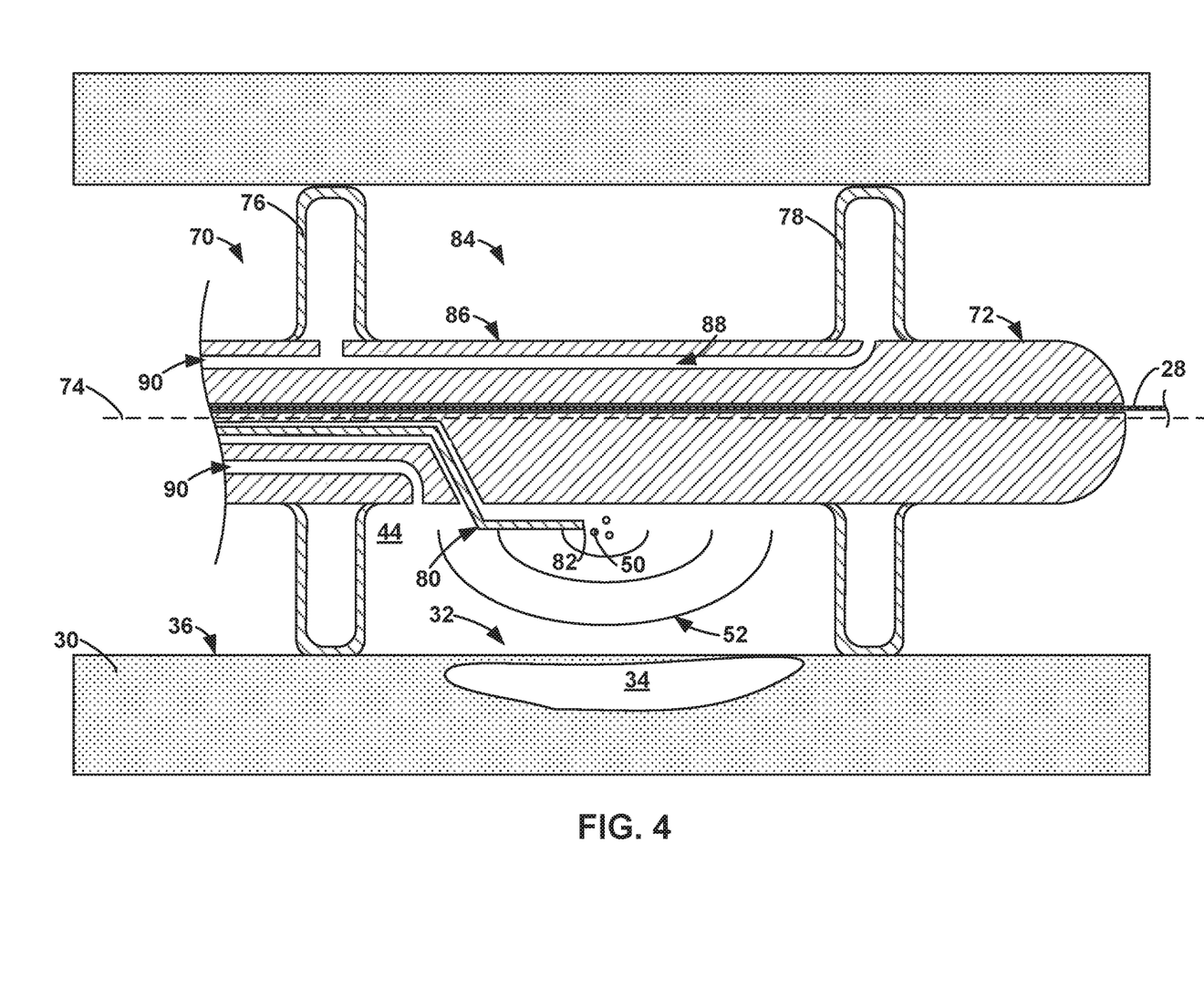
FIGS. 4-7 are enlarged cross-sectional views of example distal portions of flexible elongate members of catheters described herein.

In some examples, cavitation generator 22 may include one or more optical fiber lasers. FIG. 4 is a schematic cross-sectional view of a distal portion 70 of a flexible elongate member 72 of a catheter (e.g., catheter 10 of FIG. 1) taken along longitudinal axis 74 of flexible elongate member 72. Like FIG. 2, FIG. 4 illustrates a flexible elongate member 72 with its distal portion 70 being deployed within a vessel 30 of a patient that has a target treatment site 32 containing a calcified lesion 34 on or embedded within the wall 36 of vessel 30. Elongate member 72 includes a first balloon portion 76, a second balloon portion 78, and a cavitation generator that includes an optical fiber laser 80. Optical fiber laser 80 has a distal end 82 positioned within the cavity 84 formed between the exterior surfaces of first and second balloon portions 76, 78 and vessel wall 36.

First and second balloon portions 76, 78 may be substantially similar to first and second balloon portions 18, 20 described above with respect to FIG. 2. In some examples, first and second balloon portions 76, 78 may be fluidically connected by a connective lumen 88 formed by a connective segment 86 such that first and second balloon portions 76, 78 are in fluid connection and can be filled via lumen 90 with one of supply tubes 26. In other examples, first and second balloon portions 76, 78 may be independently filled via different lumens and/or may be constructed from portions of the same or different balloons.

Once first and second balloon portions 76, 78 have been inflated to engage with vessel wall 36 to define cavity 84. Cavity 84 may be formed by vessel wall 36 and the exterior surfaces of first and second balloon portions 76, 78 when first and second balloon portions 76, 78 are inflated in vessel 30 and contact with vessel wall 36. Fluid 44 may be contained within cavity 84 by the vessel wall 36 and the exterior surfaces of first and second balloon portions 76, 78 such that fluid is in direct contact with vessel wall 36.

In some examples, elongate member 72 may include a lumen 92 used to aspirate fluid from and/or fill cavity 84 with fluid 44. Optical fiber laser 80 may be positioned in cavity 84 such that distal end 82 of the laser is within cavity 84, exterior to both first and second balloon portions 76, 78 and in direct contact with fluid 44. In some examples, optical fiber laser 80 may be fixed (e.g., non-movable) relative to flexible elongate member 72 while in other examples, optical fiber laser 80 may be moveable relative to flexible elongate member 72 to allow a clinician to reposition distal end 82 within cavity 84 without needing to move elongate member 72 relative to vessel wall 36. Additionally or alternatively, the mobility of optical fiber laser 80 within cavity 84 may allow the clinician to reposition where cavitation occurs within cavity 84 such as, for example, having the cavitation occur closer to target treatment site 32.

An external energy source (not shown) is configured to generate and deliver photonic energy to fluid 44 within cavity 84 to rapidly heat portion of fluid 44 to generate a steam/plasma bubbles 50 within fluid 44 that represent relatively low-pressure pockets of vapor. For example, the external energy source may be optically coupled to optical fiber laser 80, and may deliver photonic energy to distal end 82 of optical fiber laser 80 through the length of optical fiber laser 80 within elongate member 72. The low-pressure steam/plasma bubbles 50 eventually collapse in on themselves due to the relatively high pressure of the surrounding fluid 44 to release a large amount of energy in the form of a high-energy pressure pulse wave 52 within fluid 44. Pressure pulse waves 52 propagate through fluid 44 where they impact vessel wall 36 transmitting the mechanical energy of pressure pulse waves 52 into the tissue of vessel 30 and calcified lesion 34. The energy transmitted to calcified lesion 34 may cause the lesion to fracture or break apart allowing vessel 30 to be subsequently expanded (e.g., via balloon expansion) to a normal flow diameter.

In some examples, the photonic energy delivered to fluid 44 via optical fiber laser 80 may be provided by an energy source similar to that shown in FIG. 3, except that the energy source is configured to transmit photonic, e.g., light energy as opposed to electrical energy. For example, the energy source used to power optical fiber laser 80 may include a pulse generator capable of delivering a single photonic pulse or multiple photonic pulses to optical fiber laser 80. Each photonic pulse may have an energy input between 5 millijoules (mJ) to about 15 mJ. The duration of the photonic pulses delivered may be relatively short having a pulse width between about 1 nanosecond and about 20 nanoseconds (e.g., about 6 nanoseconds). In some examples, the pulse generator may deliver a plurality of photonic pulses, each having a pulse width between about 1 nanosecond and about 20 nanoseconds, at a frequency of about 10 milliseconds to about 10 seconds.

Additionally, or alternatively, cavitation generator 22 may include one or more piezoelectric transducers (e.g., similar to electrical conductors 56A, 56B of FIG. 2). The piezoelectric transducers may be powered using electrical energy supplied through one or more conductors and an energy source external to the patient (e.g., similar to energy source 60 of FIG. 3). The one or more piezoelectric transducers may convert the electrical energy into ultrasonic energy that is used to heat fluid 44 within the cavity formed by the first and second balloon portions (e.g., cavity 42 of FIG. 2). The ultrasonic energy may rapidly heat portion of fluid 44 to generate a steam/plasma bubbles 50 within fluid 44 that represent relatively low-pressure pockets of vapor. As the heat of the steam/plasma bubbles 50 is dissipated by the surrounding fluid 44, low-pressure steam/plasma bubbles 50 will eventually collapse in on themselves due to the relatively high pressure of the surrounding fluid 44 to release a large amount of energy in the form of a high-energy pressure pulse wave 52 within fluid 44. As described above, pressure pulse waves 52 propagate through fluid 44 where they impact vessel wall 36 transmitting the mechanical energy of pressure pulse waves 52 into the tissue of vessel 30 and calcified lesion 34. The energy transmitted to calcified lesion 34 may cause the lesion to fracture or beak apart allowing vessel 30 to be subsequently expanded (e.g., via balloon expansion) to a normal flow diameter.

Figure 5:
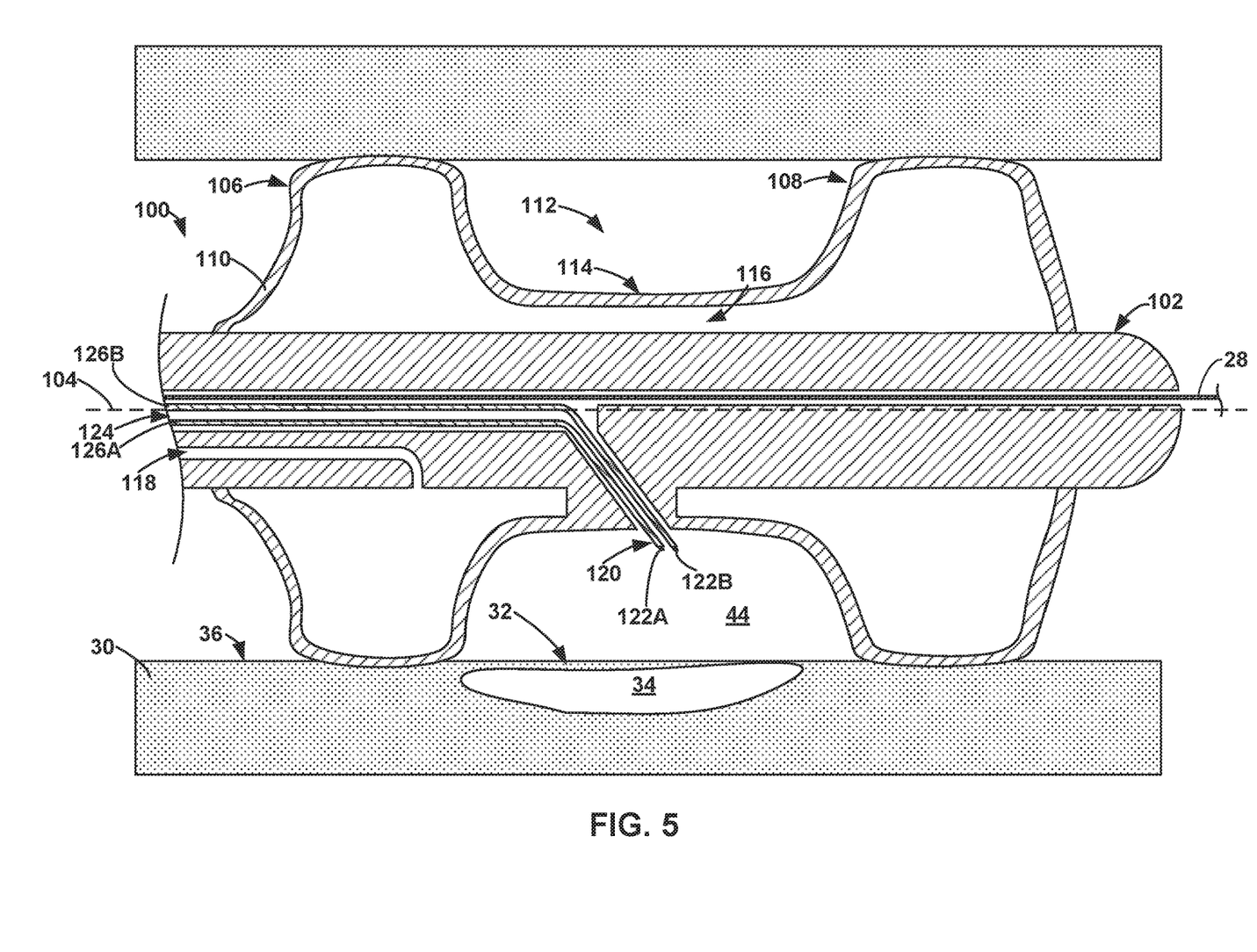

FIG. 5 is a schematic cross-sectional view of a distal portion 100 of another example flexible elongate member 102 of a catheter (e.g., catheter 10 of FIG. 1) taken along longitudinal axis 104 of flexible elongate member 102.

Distal portion 100 includes a first balloon portion 106 and second balloon portion 108 connected to flexible elongate member 102 and a cavitation generator 120 that includes a plurality of electrodes 122A, 122B in direct contact with fluid 44 contained within cavity 112. Fluid 44 within cavity 112 is in direct contact with vessel wall 36. Cavity 112 is formed by vessel wall 36 and the exterior surfaces of first and second balloon portions 106, 108 when first and second balloon portions 106, 108 are inflated in vessel 30 and contact with vessel wall 36. Fluid 44 may be contained within cavity 112 by the vessel wall 36 and the exterior surfaces of first and second balloon portions 106, 108.

Cavitation generator 120 including substantially similar to cavitation generator 22 described above with respect to FIG. 2. For example, cavitation generator 120 may include a plurality of electrodes 122A, 122B which are positioned within cavity 142 in direct contact with fluid 44. In some examples, electrodes 122A, 122B may be provided through a common lumen 124 of elongate member 102, which may also be shared with guidewire 28 in some examples. In such examples, the one or more conductors 126A, 126B providing electrical energy to electrodes 122A, 122B may be electrically insulated from one another using, for example, an electrically insulative sheath material. In other examples, one or more conductors 126A, 126B may be electrically insulated from one another using different lumens within elongate member 102. Additionally or alternatively, one of the electrodes may be provided by a portion of guidewire 28. In other examples, cavitation generator 120 may include an optical fiber laser substantially similar to optical fiber laser 80 described above with respect to FIG. 4, or may include one or more piezoelectric transducers as described above. The details of cavitation generator 120 will not be repeated here for simplicity.

As shown in FIG. 5, first and second balloon portions 106, 108 are different lobes of a single balloon 110 that are connected to flexible elongate member 102. In some examples, balloon 110 may define dumbbell shape (also referred to herein as a dog bone shape in some examples), and first and second balloon portions 106, 108 may correspond to respective lobes of the dumbbell shape.

Balloon 110 also includes a connective segment 114 that defines a channel 116 that fluidically connects first balloon portion 106 and second balloon portion 108. In some examples, connective segment 114 may be formed by a portion of balloon 110 that remains separated from elongate member 102 to define channel 116, which may be any suitable size and shape. In some examples, connective segment 114 of balloon 110 may be partially or completely secured to elongate member 102 such that only the expandable first and second balloon portions 106, 108 remain separated from flexible elongate member 102. In such examples first and second balloon portions 106, 108 will inflate upon expansion while connective segment 114 may remain secured to elongate member 102.

Balloon 110 including first and second balloon portions 106, 108 may be inflated to an expanded state using a fluid supplied by one or more lumens 118 and supply tubes 26 of catheter 10. Once expanded, first and second balloon portions 106, 108 may engage with vessel wall 36 to define cavity 112 that lies between and exterior to first and second balloon portions 106, 108. As described above with respect to cavity 42 (FIG. 2), cavity 112 may be aspirated and/or filled with fluid 44 via a lumen (not shown) of flexible elongate member 102 that opens to cavity 112. In some such examples, the lumen may extend through balloon 110 but remain fluidically separated from balloon 110.

In some examples, a treatment balloon may be used before or after the cavitation procedure to dilate vessel 30 and increase the flow diameter of the vessel. The treatment balloon can be provided by a separate catheter that is introduced into vessel 30 after the cavitation catheter (e.g., catheter 10) is removed from vessel 30. In other examples, the cavitation catheter, e.g., catheter 10, can include a treatment balloon positioned over the flexible elongated member, e.g., flexible elongated member 12 of FIG. 1. In some examples, the treatment balloon may be inflatable within cavity 42 formed by first and second balloon portions 18, 20 to expand vessel 30 after delivery of the pressure pulse wave by a cavitation generator of the catheter, e.g., cavitation generator 22 of FIG. 1, or may be positioned over a different portion of elongate member 12 and is moved in position of target treatment site 32 after the cavitation procedure has been performed and first and second balloon portions 18, 20 have been deflated.

Figure 6:
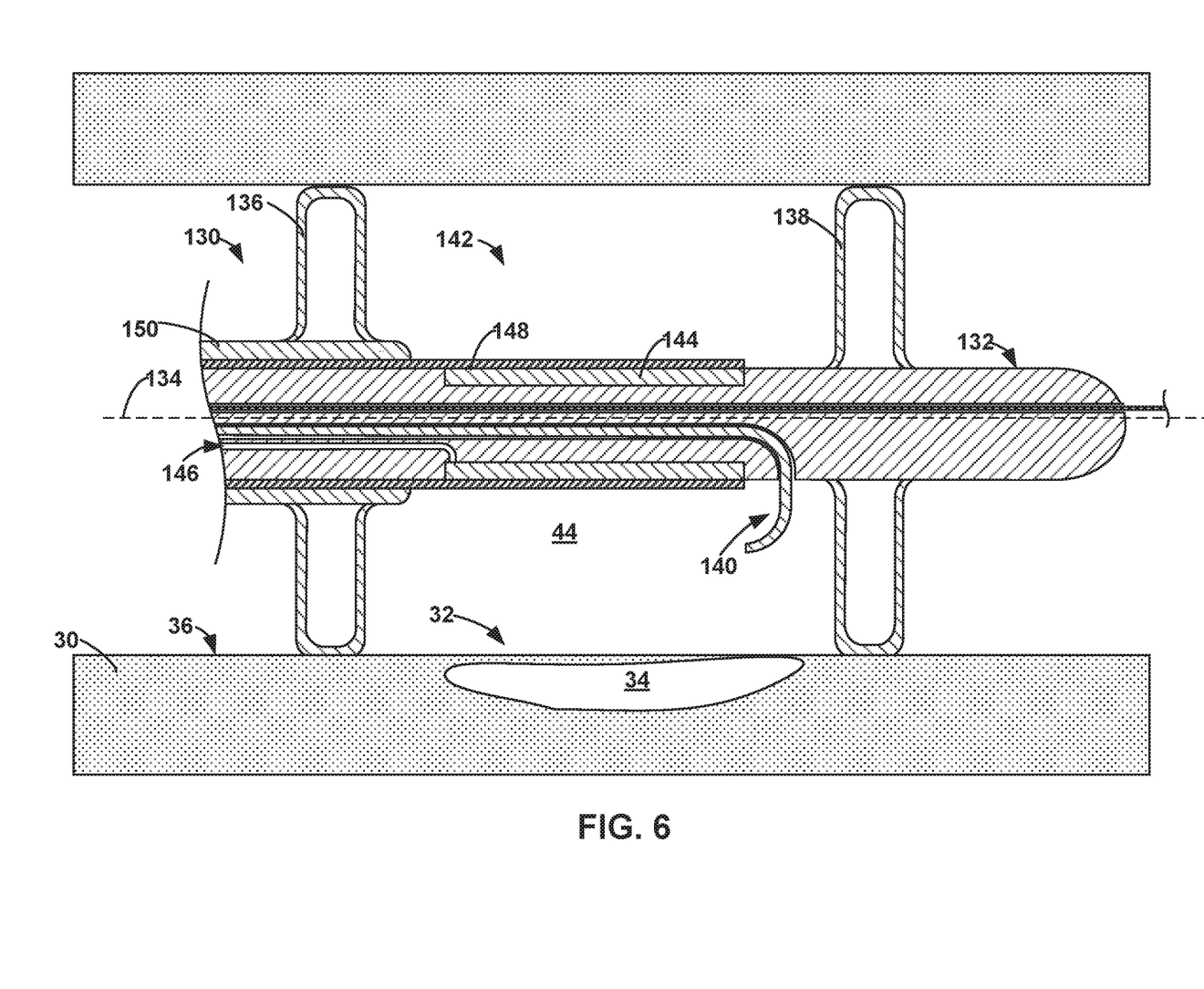
Figure 7:
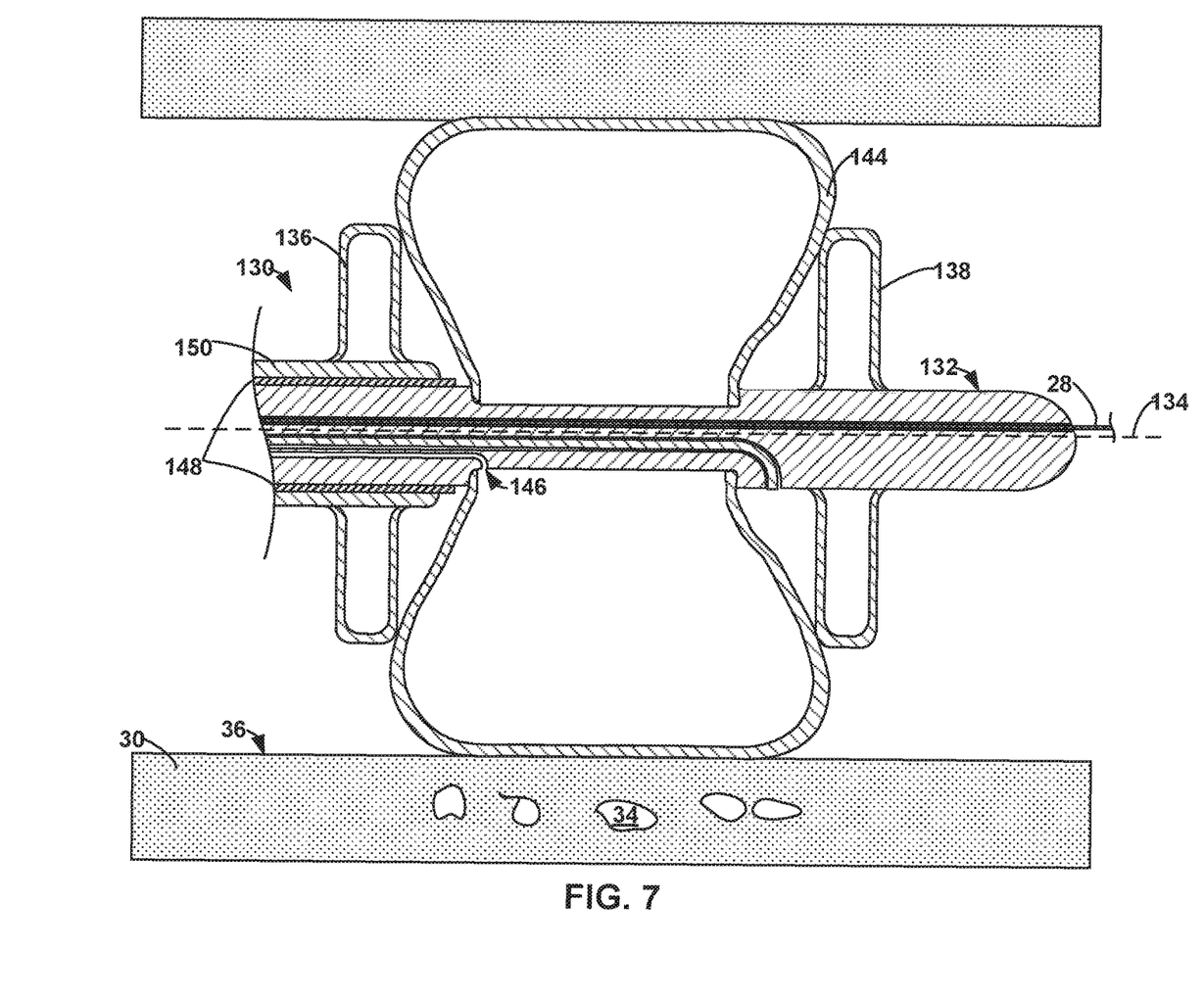

FIGS. 6 and 7 are cross-sectional views of a distal portion 130 of another example flexible elongate member 132 of a catheter (e.g., catheter 10 of FIG. 1) taken along longitudinal axis 134 of flexible elongate member 132. Distal portion 130 includes a first balloon portion 136 and second balloon portion 138 connected to flexible elongate member 132 and a cavitation generator 140 (e.g., including an optical fiber laser, plurality of electrodes, or one or more piezoelectric transducers) in direct contact with fluid 44 contained within cavity 142 formed by vessel wall 36 and the exterior surfaces of first and second balloon portions 136, 138 when first and second balloon portions 136, 138 are inflated in vessel 30. The various details of first balloon portion 136, second balloon portion 138, and cavitation generator 140 may be substantially similar to one or more of the example medical devices described above with respect to FIGS. 2-5 and will not be repeated here.

The catheter shown in FIG. 6 includes a treatment balloon 144 mechanically connected to flexible elongate member 132 and positioned between first and second balloon portions 136, 138. FIG. 6 shows treatment balloon 144 in a non-expanded state. Treatment balloon 144 may be in the non-expanded state during a cavitation procedure. After the cavitation procedure has caused calcified lesion 34 to fracture or break apart using cavitation generator 140, treatment balloon 144 may be inflated to an expanded state (FIG. 7) via one or more lumens 146 defined by flexible elongate member 132 and supply tubes 26. Once inflated, treatment balloon 144 may engage vessel wall 36 and forcibly expand the diameter of vessel wall 36. In some examples, the cavitation procedure and expansion of treatment balloon 144 may be repeated multiple times (e.g., form cavity 142, cavitate fluid 44 within cavity 142, expand vessel wall 36 via treatment balloon 144, reform cavity 142 and repeat the process) to expand the diameter of vessel wall 36 using an incremental process.

In some examples, treatment balloon 144 may include a therapeutic agent such as one or more of an anti-restenotic agent, an anti-proliferative agent, an anti-inflammatory agent, or other therapeutic agent over an exterior surface of treatment balloon 144. When treatment balloon 144 is expanded and in contact with vessel wall 36, as shown in FIG. 7, the therapeutic agent may contact vessel wall 36 and be absorbed by vessel 30 to help prevent restenosis of vessel 30 or otherwise treat vessel 30. Example therapeutic agents may include, anti-proliferative agents such as paclitaxel, paclitaxel derivatives, or limus derivatives (e.g., sirolimus, everolimus, and the like), or anti-inflammatory agents such as non-steroid or steroid anti-inflammatory agents such as -COX inhibitors or glucocorticoids. Additionally or alternatively, one or more therapeutic agents may be delivered to the vessel 30 via peripheral infusion through a lumen of elongate member 132 directly into cavity 142.

In some examples, a catheter may also include a retractable sheath 148 disposed over treatment balloon 144 during the cavitation procedure. Retractable sheath 148 may help protect the structural integrity of treatment balloon 144 and/or the integrity of a therapeutic agent applied to balloon 144 or otherwise carried by balloon 144 during the cavitation procedure. Additionally or alternatively, retractable sheath 148 may prevent the therapeutic coating from diffusing into fluid 44 prior to the expansion of treatment balloon 144. Once the cavitation procedure has been completed, retractable sheath 148 may be withdrawn distally (e.g., withdrawn proximally into outer sheath 150 that includes first balloon portion 136 attached thereto) to expose treatment balloon 144.

Figure 8:
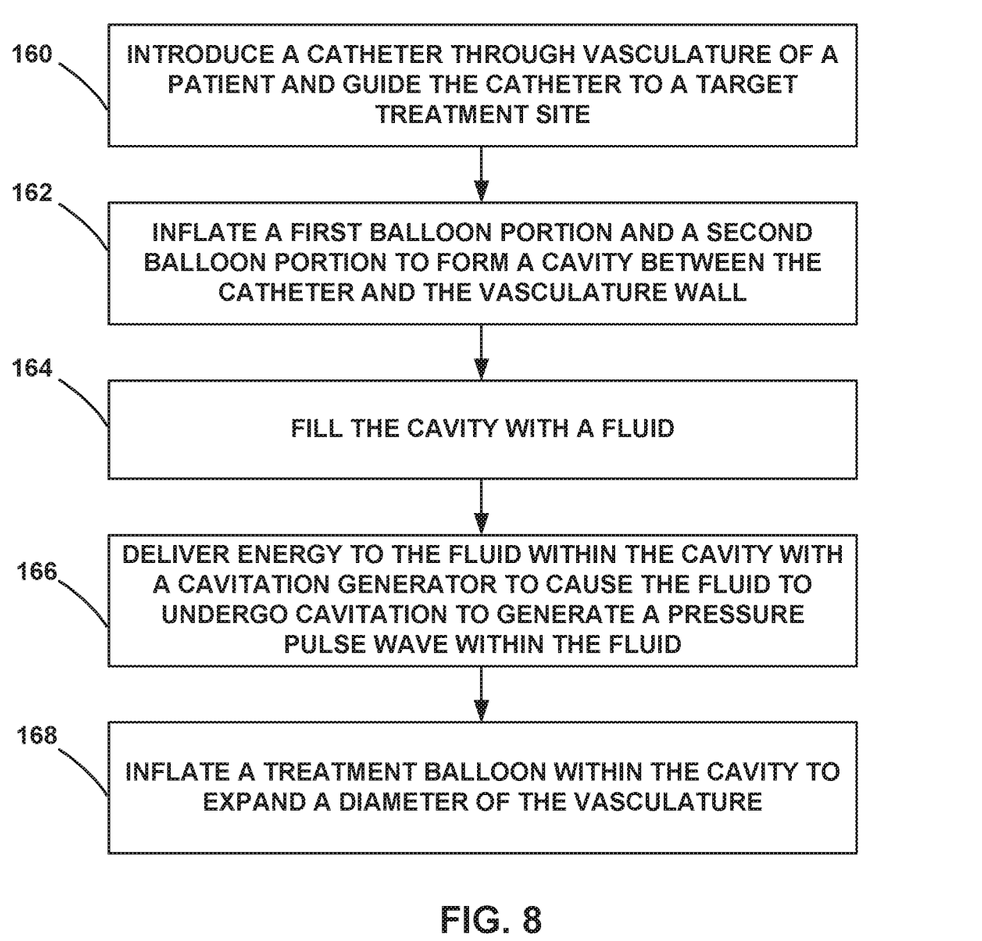
FIG. 8 is a flow diagram of an example technique of using the medical devices described herein.

FIG. 8 is a flow diagram of an example technique of using catheter 10 described above. The techniques of FIG. 8 are described with reference to the various aspects of the devices of FIGS. 1-7 for illustrative purposes, however, such descriptions are not intended to be limiting and the techniques of FIG. 8 may be used with other catheters or catheter 10 of FIGS. 1-7 may be used for other applications.

The technique of FIG. 8 includes introducing a catheter 10 including a flexible elongate member 12 into a vessel 30 of a patient and guide a distal portion 16B of catheter 10 to a target treatment site 32 adjacent to a calcified lesion 34 (160), and inflating first and second balloon portions 18, 20 to the respective expanded state to form a cavity 42 between external surfaces of balloons 18, 20, catheter 10 and vessel wall 36 (162). As described above, distal portion 16B may include a first and second balloon portions 18, 20 connected to elongate member 12 and separated by a distance such that such when inflated to engage with vessel wall 36, first balloon portion 18 occludes a proximal portion of vessel 30 proximal to target treatment site 32 and second balloon portion 18 occludes a distal portion of vessel 30 distal to target treatment site 32 to form cavity 42 that is exterior to the first and second balloon portions 18, 20.

In some examples, first and second balloon portions 18, 20 may be independently expanded using different lumens 38, 40 to expand first and second balloon portions 18, 20. In some such examples, first and second balloon portions 18, 20 may be sequentially expanded in an order that follows the direction of blood flow within vessel 30. For example, if blood flows in the x-axis direction of FIG. 2, first balloon portion 18 may be inflated prior to inflating second balloon portion 20. In some examples, sequentially inflating first and second balloon portions 18, 20 in such a manner may assist with removing blood from cavity 42 by allowing blood to continue to flow from cavity 42 prior to second balloon portion 20 being inflated.

During or after first and second balloon portions 18, 20 have been inflated to engage vessel wall 36, cavity 42 may be filled with fluid 44 (164). In some examples, cavity 42 may be filled with fluid 44 using a lumen 46 defined by elongate member 12 configured to provide access to cavity 42. Fluid 44 may include any suitable fluid capable of undergoing a cavitation procedure. In some examples, cavity 42 may be aspirated (e.g., using lumen 46) prior to filling cavity 42 with fluid 44 and/or after the cavitation procedure to remove fluid 44 from cavity 42 before deflating first and second balloon portions 18, 20.

The technique of FIG. 8 also includes delivering energy 48 to fluid 44 within cavity 42 using a cavitation generator 22 to cause fluid 44 to undergo cavitation to generate a pressure pulse wave 52 within fluid 44 (166). As described above, cavitation generator 22 may include, for example, a plurality of electrodes 54A, 54B, an optical fiber laser 80, or one or more piezoelectric transducers designed to transmit energy 48 to fluid 44 (e.g., electrical, photonic, or ultrasonic energy) that rapidly heats a portion of fluid 44 to produce short-lived gaseous steam/plasma bubbles 50 within fluid 44. The steam/plasma bubbles 50 may represent relatively low-pressure pockets of vapor generated from the surrounding fluid 44. The low-pressure steam/plasma bubbles 50 eventually collapse in on themselves due to the relatively high pressure of the surrounding fluid 44. As steam/plasma bubbles 50 collapse, the bubbles release a large amount of energy in the form of a high-energy pressure pulse wave 52 within fluid 44 that propagate through fluid 44 where they impact vessel wall 36 transmitting the mechanical energy of pressure pulse wave 52 into the tissue of vessel 30 and calcified lesion 34. The energy transmitted to calcified lesion 34 may cause the lesion to fracture or beak apart. This cavitation treatment of calcified lesion 34 may be used in conjunction with a treatment balloon 144 to help open-up vessel 30 of the patient, restoring the vasculature to a normal flow diameter.

As described above, in examples in which cavitation generator 22 includes a plurality of electrodes 54A, 54B, cavitation generator 22 may deliver an electrical signal between two of the plurality of electrodes 54A, 54B or between one or both electrodes 54A, 54B and an electrode defined by a guidewire, or using other electrodes within cavity 42, to generate a corona, an electrical arc, a spark or the like between the electrodes in contact with fluid 44. The electrical signal may be a continuous wave signal or in the form of a plurality of pulses, and may have any suitable electrical signal parameters for creating the cavitation. For example, the electrical signal may have an amplitude of about 500 volts (V) to about 4000 V, a pulse width of about 1 microsecond to about 5 microseconds, and a frequency of about 0.5 Hertz (Hz) to about 5 Hz.

In examples in which cavitation generator 22 includes an optical fiber laser 80, cavitation generator 22 may deliver photonic energy via optical fiber laser 80 to a distal end 82 in contact with fluid 44 to cause fluid 44 to generate steam/plasma bubbles 50. The duration of the photonic pulse delivered may be relatively short having a pulse width between about 1 nanosecond and about 20 nanoseconds (e.g., about 6 nanoseconds). In some examples, the pulse generator may deliver a plurality of photonic pulses, each having a pulse width between about 1 nanosecond and about 20 nanoseconds, at a frequency of about 10 milliseconds to about 10 seconds to create a series of pressure pulse waves 52.

In some examples, the technique of FIG. 8 also includes inflating treatment balloon 144 within cavity 142 to expand a diameter of vessel 30 (168). However, in other examples, the technique of FIG. 8 does not include inflating treatment balloon 144. Once the cavitation procedure has fractured or broken apart calcified lesion 34, treatment balloon 144 may be inflated to an expanded state via one or more lumens 146 defined by flexible elongate member 132 and supply tubes 26. Once inflated, treatment balloon 144 may engage vessel wall 36 and forcibly expand the diameter of vessel wall 36.

If the catheter includes retractable sheath 148, retractable sheath 148 may be withdrawn proximally to expose treatment balloon 144 prior to inflating treatment balloon 144.

After vessel 30 is expanded to increase a flow diameter using the technique of FIG. 8, treatment balloon 144, and first and second balloon portions 136, 138 may be deflated and catheter 10 may be withdrawn from vessel 30.

Various examples have been described. These and other examples are within the scope of the following claims.

What is claimed is:

1. A medical device comprising:
a flexible elongate member comprising a distal portion configured to be navigated though vasculature of a patient to a target treatment site;
a first balloon portion connected to the flexible elongate member, wherein the first balloon portion is inflatable to an expanded state to occlude a proximal portion of the vasculature proximal to the target treatment site;
a second balloon portion connected to the flexible elongate member, wherein the second balloon portion is inflatable to an expanded state to occlude a distal portion of the vasculature distal to the target treatment site, and wherein when the first and second balloon portions are in the respective expanded states within the vasculature, a cavity is defined between the flexible elongate member and the target treatment site, the cavity being exterior to the first and second balloon portions;
a cavitation generator configured to deliver energy to a fluid within the cavity to cause the fluid to undergo cavitation to generate a pressure pulse wave within the fluid; and
a treatment balloon positioned over the flexible elongate member, the treatment balloon being inflatable within the cavity to expand the vasculature after delivery of the energy by the cavitation generator.

2. A medical device comprising:
a flexible elongate member comprising a distal portion configured to be navigated though vasculature of a patient to a target treatment site;
a first balloon portion connected to the flexible elongate member, wherein the first balloon portion is inflatable to an expanded state to occlude a proximal portion of the vasculature proximal to the target treatment site;
a second balloon portion connected to the flexible elongate member, wherein the second balloon portion is inflatable to an expanded state to occlude a distal portion of the vasculature distal to the target treatment site, and wherein when the first and second balloon portions are in the respective expanded states within the vasculature, a cavity is defined between the flexible elongate member and the target treatment site, the cavity being exterior to the first and second balloon portions;
a cavitation generator configured to deliver energy to a fluid within the cavity to cause the fluid to undergo cavitation to generate a pressure pulse wave within the fluid, wherein the cavitation generator comprises a plurality of electrodes configured to deliver an electrical signal to the fluid within the cavity to induce the cavitation within the fluid; and
a guidewire, wherein the flexible elongate member defines a lumen configured to receive the guidewire, and wherein the guidewire forms an electrode of the plurality of electrodes.

3. The medical device of claim 1, wherein the cavitation generator is configured to deliver the energy to the fluid within the cavity to heat the fluid to produce short-lived gaseous bubbles that collapse to generate the pressure pulse wave within the fluid.

4. The medical device of claim 1, further comprising a delivery catheter configured to deliver the fluid to the cavity.

5. The medical device of claim 4, wherein the delivery catheter is configured to aspirate the cavity prior to delivering the fluid.

6. The medical device of claim 1, further comprising a connective segment defining a connective lumen, the connective lumen providing a fluid connection between the first and second balloon portions.

7. The medical device of claim 6, wherein the medical device comprises a single balloon comprising the first balloon portion, the second balloon portion, and the connective segment, the single balloon having a dumbbell shape, the first and second balloon portions corresponding to lobes of the dumbbell shape.

8. The medical device of claim 1, further comprising a treatment balloon positioned over the flexible elongate member, the treatment balloon being inflatable within the cavity to expand the vasculature after delivery of the pressure pulse wave by the cavitation generator.

9. The medical device of claim 1, further comprising a retractable sheath disposed over the treatment balloon, the retractable sheath being configured to be retracted to expose the treatment balloon after the delivery of the pressure pulse wave by the cavitation generator.

10. The medical device of claim 1, wherein the treatment balloon comprises at least one of an anti-restenotic agent, an anti-proliferative agent, or an anti-inflammatory agent.

11. The medical device of claim 1, wherein the cavitation generator comprises a plurality of electrodes configured to deliver an electrical signal to the fluid within the cavity to induce the cavitation within the fluid.

12. The medical device of claim 11, further comprising a guidewire, wherein the flexible elongate member defines a lumen configured to receive the guidewire, and wherein the guidewire forms an electrode of the plurality of electrodes.

13. The medical device of claim 2, wherein the flexible elongate member defines at least one opening through a sidewall of the flexible elongate member, wherein the at least one opening exposes an electrically conductive surface of the guidewire to the fluid within the cavity, and wherein the electrically conductive surface of the guidewire forms an electrode of the plurality of electrodes.

14. The medical device of claim 11, wherein at least two of the plurality of electrodes are moveable relative to each other.

15. The medical device of claim 1, wherein the cavitation generator comprises an optical fiber laser or a piezoelectric transducer.

16. The medical device of claim 1, wherein at least a portion of the cavitation generator is positioned within the cavity and exterior to the first and second balloon portions.

17. The medical device of claim 1, further comprising a signal generator configured to generate and deliver the energy to the fluid within the cavity via the cavitation generator.

18. The medical device of claim 17, wherein the signal generator is configured to deliver a plurality of energy pulses in the form of electrical or photonic energy, the energy pulses having a pulse width of about between about 1 nanosecond and about 20 nanoseconds.

* * * * *